(12) United States Patent
Redda et al.

(10) Patent No.: US 8,889,713 B1
(45) Date of Patent: Nov. 18, 2014

(54) N-SUBSTITUTED TETRAHYDROISOQUINOLINE BENZAMIDES/BENZENE SULFONAMIDES AS ANTI-CANCER AGENTS

(71) Applicant: Florida A&M University, Tallahassee, FL (US)

(72) Inventors: Kinfe Ken Redda, Tallahassee, FL (US); Madhavi Gangapuram, Tallahassee, FL (US)

(73) Assignee: Florida A&M University, Tallahassee, FL (US)

( * ) Notice: Subject to any disclaimer, the term of this patent is extended or adjusted under 35 U.S.C. 154(b) by 0 days.

(21) Appl. No.: 13/960,886

(22) Filed: Aug. 7, 2013

(51) Int. Cl.
  *C07D 217/08* (2006.01)
  *A61K 31/472* (2006.01)
  *C07D 417/12* (2006.01)

(52) U.S. Cl.
  CPC ............ *C07D 217/08* (2013.01); *C07D 417/12* (2013.01)
  USPC .......................................... 514/310; 546/143

(58) Field of Classification Search
  None
  See application file for complete search history.

(56) References Cited

U.S. PATENT DOCUMENTS 8,546,426 B2 * 10/2013 Redda et al. .................. 514/310

* cited by examiner

*Primary Examiner* — Zinna Northington Davis
(74) *Attorney, Agent, or Firm* — Thomas|Horstemeyer, LLP

(57) ABSTRACT

The compounds herein disclosed are N-substituted tetrahydroisoquinoline benzamide and benzene sulfonamide compounds that have modifications on the phenyl rings by introducing groups with various electronic properties. These derivatives of N-substituted tetrahydroisoquinoline compounds have been shown to have anti-proliferative activity against cells. In particular, the compounds have been found to be effective in inhibiting the proliferation of cancer cells, such as cancer cells that originated in breast tissue. Additionally, it has been shown that the novel compounds have $IC_{50}$ values against the breast cancer cells that are 6- to 10-fold less than the $IC_{50}$ of Tamoxifen.

15 Claims, 3 Drawing Sheets

N-SUBSTITUTED TETRAHYDROISOQUINOLINE BENZAMIDES/BENZENE SULFONAMIDES AS ANTI-CANCER AGENTS

STATEMENT REGARDING FEDERALLY SPONSORED RESEARCH OR DEVELOPMENT

This invention was made with government support under Grant No. Research RR 03020 Funded by the National Institutes of Health National Center for Research Resources (NCRR) Research Center in Minority Institutions (RCMI) Program. The government has certain rights in the invention

TECHNICAL FIELD

The present disclosure is generally related to N-substituted tetrahydroisoquinoline benzamide and benzene sulfonamide compounds and their use in modulating the proliferation of transformed (cancer) cells.

BACKGROUND

Cancer is a disease in which cells in the body grow out of control. Cancer and cancer cells are typically named according to the tissue in which the cells start; e.g. when originating in the breast, it is called breast cancer. Breast cancer is the second leading cause of cancer-related deaths in women today and is the most common cancer among women, excluding non-melanoma skin cancers. In 2009, an estimated 192,370 new cases of invasive breast cancer were diagnosed among women, as well as an estimated 62,280 additional cases of in situ breast cancer. In 2009, approximately 40,170 women were expected to die from breast cancer.

The nuclear receptor, estrogen receptor (ER) and progesterone receptor (PR) and their associated steroid hormones, are known to play essential roles in the growth of breast tumors, and their status is also employed as diagnostic indicators for endocrine responsiveness and tumor recurrence. The estrogen receptors (ERs) are attractive targets in the treatment of breast cancer and the development of receptor-based breast cancer imaging agents for diagnostic use in biomedical imaging technique positron emission tomography (PET).

Ecteinascidin-743 (ET-743) is a marine tetrahydroisoquinoline (THIQ) alkaloid isolated from the tunicate *Ekteinascidia turbinata* with a potent cytotoxic activity against a variety of tumor cell lines in vitro and against several rodent tumors and human tumor xenografts in vivo. Tetrahydroisoquinoline natural products have been shown to exhibit biological activity that renders them as potential pharmaceutical agents. The tetrahydroisoquinoline family of alkaloids includes potent cytotoxic agents that display a range of biological properties such as antitumor and antimicrobial activities studied thoroughly over the past 25 years, starting with the isolation of naphthyndinomycin in 1974. 1-Methyl-1,2,3,4-tetrahydraisoquinoline (1-MeTIQ) is considered to be a possible endogenous Parkinsonism-preventing agent that is present in the mouse, rat, monkey and human.

SUMMARY

Briefly described, this disclosure provides, among others, embodiments of a compound having the structure of formula I:

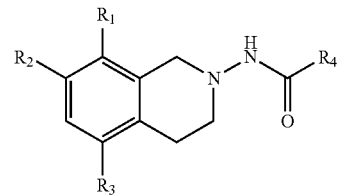

wherein: $R_1$ can be H or a halogen; $R_2$ can be H, an hydroxyl, or a carboxyalkyl; $R_3$ can be H, a halogen, or a carboxyalkyl, and wherein, when $R_3$ is a carboxyalkyl, $R_1$ is H; and $R_4$ is an alkylaryl or a benzothiazole; or a salt thereof.

In some embodiments of this aspect of the disclosure, when the compound can be selected from the group consisting of:

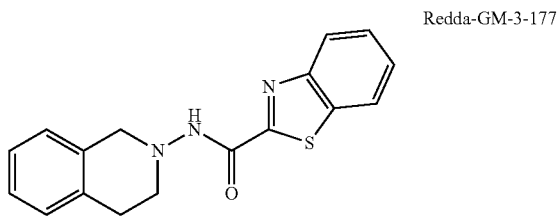
Redda-GM-3-177

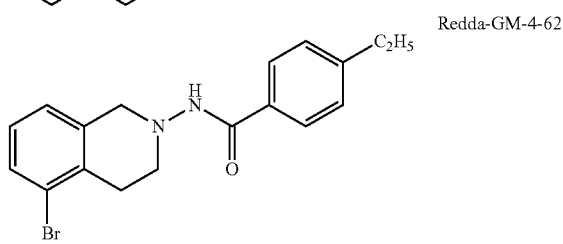
Redda-GM-4-62

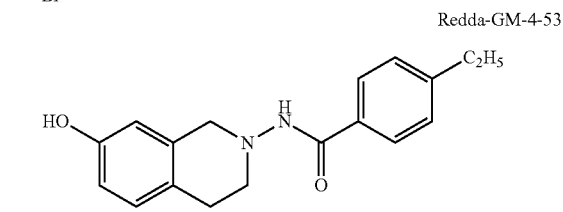
Redda-GM-4-53

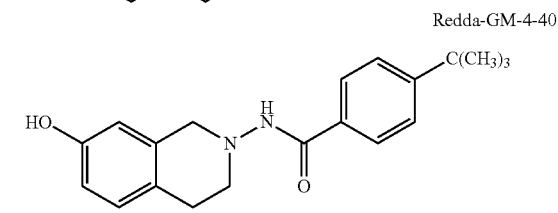
Redda-GM-4-40

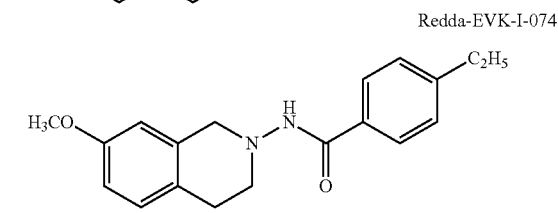
Redda-EVK-I-074

Redda-EVK-I-079

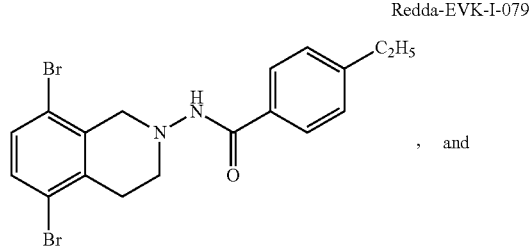

, and

Redda-EVK-I-062

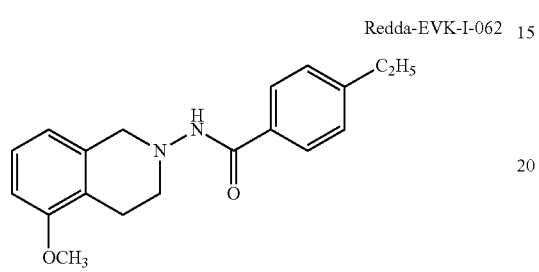

Another aspect of the disclosure encompasses embodiments of a pharmaceutically acceptable composition comprising a compound having the structure:

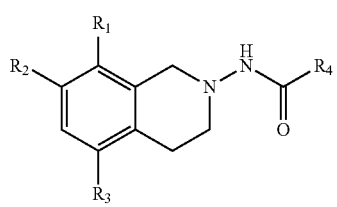

I wherein: $R_1$ can be H or a halogen; $R_2$ can be H, an hydroxyl, or a carboxyalkyl; $R_3$ can be H, a halogen, or a carboxyalkyl, and wherein, when $R_3$ is a carboxyalkyl, $R_1$ is H; and $R_4$ is an alkylaryl or a benzothiazole; or a salt thereof.

In embodiments of this aspect of the disclosure, when the compound can be selected from the group consisting of:

Redda-GM-3-177

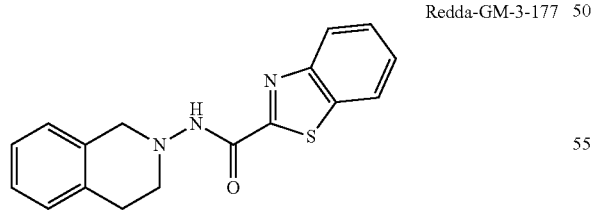

Redda-GM-4-62

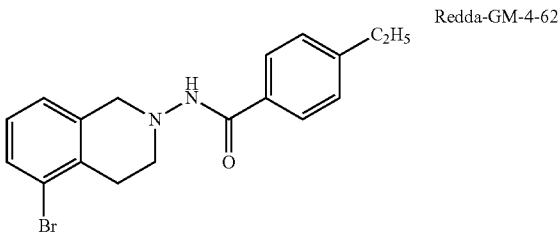

Redda-GM-4-53

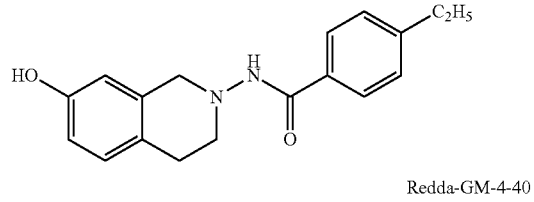

Redda-GM-4-40

Redda-EVK-I-074

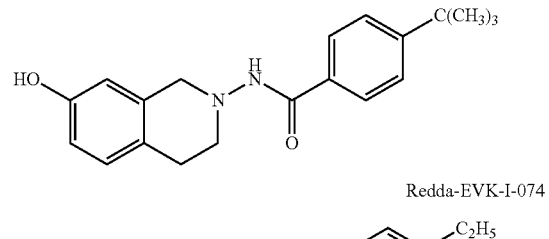

Redda-EVK-I-079

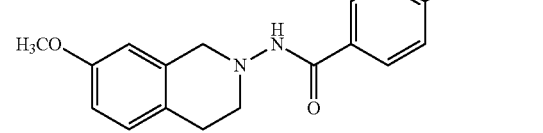

, and

Redda-EVK-I-062

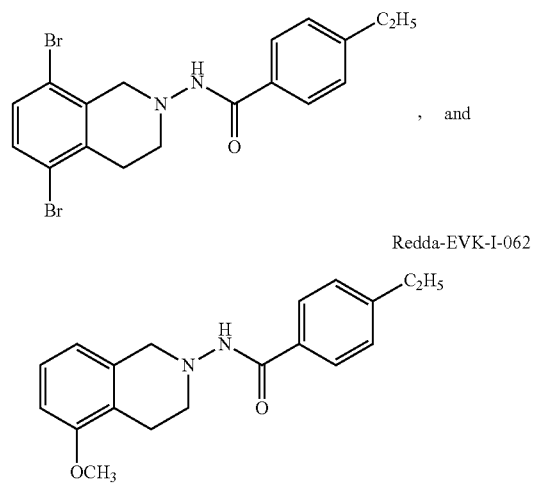

In embodiments of this aspect of the disclosure, the pharmaceutically acceptable composition can be formulated to provide an amount of the compound effective in inhibiting the proliferation of a cell cultured in vitro. In these embodiments, the cell can be a cancer cell. In some embodiments of this aspect of the disclosure, the cell can be a breast cancer cell.

In embodiments of this aspect of the disclosure, the pharmaceutically acceptable composition can be formulated to provide a therapeutically effective amount of the compound for inhibiting the proliferation of a cell in vivo. In these embodiments of this aspect of the disclosure, the cell is a cancer cell. In these embodiments of this aspect of the disclosure, the cell can be a breast cancer cell.

Still another aspect of the disclosure encompasses embodiments of a method of inhibiting the proliferation of a cell comprising contacting a cell with an effective amount of a compound having the structure:

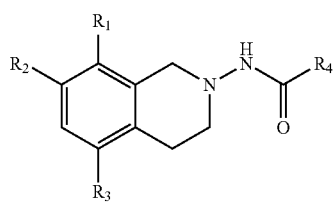

wherein:
R$_1$ is H or a halogen;
R$_2$ is H, an hydroxyl, or a carboxyalkyl;
R$_3$ is H, a halogen, or a carboxyalkyl, wherein, when R$_3$ is a carboxyalkyl, R$_1$ is H; and
R$_4$ is an alkylaryl or a benzothiazole;
or a salt thereof, and a pharmaceutically acceptable carrier, thereby reducing the proliferation rate of the cell compared to the proliferation rate of a cell not in contact with the compound.

In embodiments of this aspect of the disclosure, the compound can be selected from the group consisting of:

Redda-GM-3-177

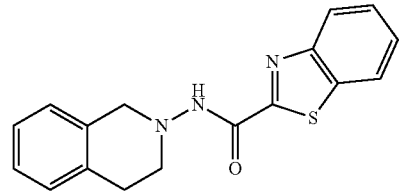

Redda-GM-4-62

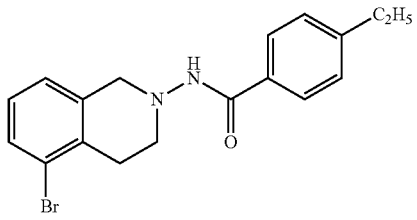

Redda-GM-4-53

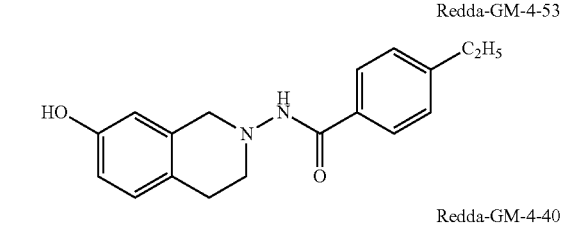

Redda-GM-4-40

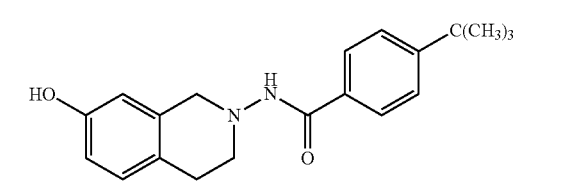

Redda-EVK-I-074

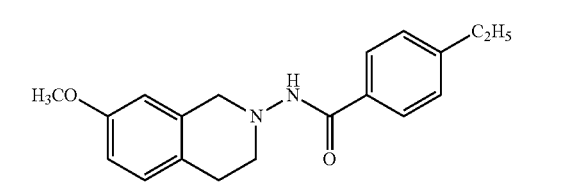

Redda-EVK-I-079

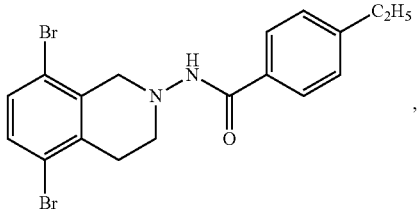

, and

Redda-EVK-I-062

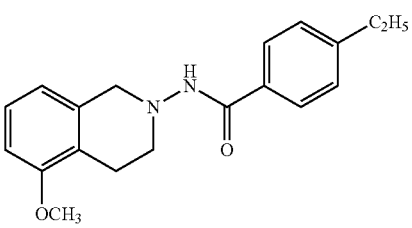

In embodiments of this aspect of the disclosure, the cell can be a breast cancer cell.

In embodiments of this aspect of the disclosure, the cell can be a cultured cell or a cell of an animal or human subject.

BRIEF DESCRIPTION OF THE DRAWINGS

Further aspects of the present disclosure will be more readily appreciated upon review of the detailed description of its various embodiments, described below, when taken in conjunction with the accompanying drawings.

Figure 1:
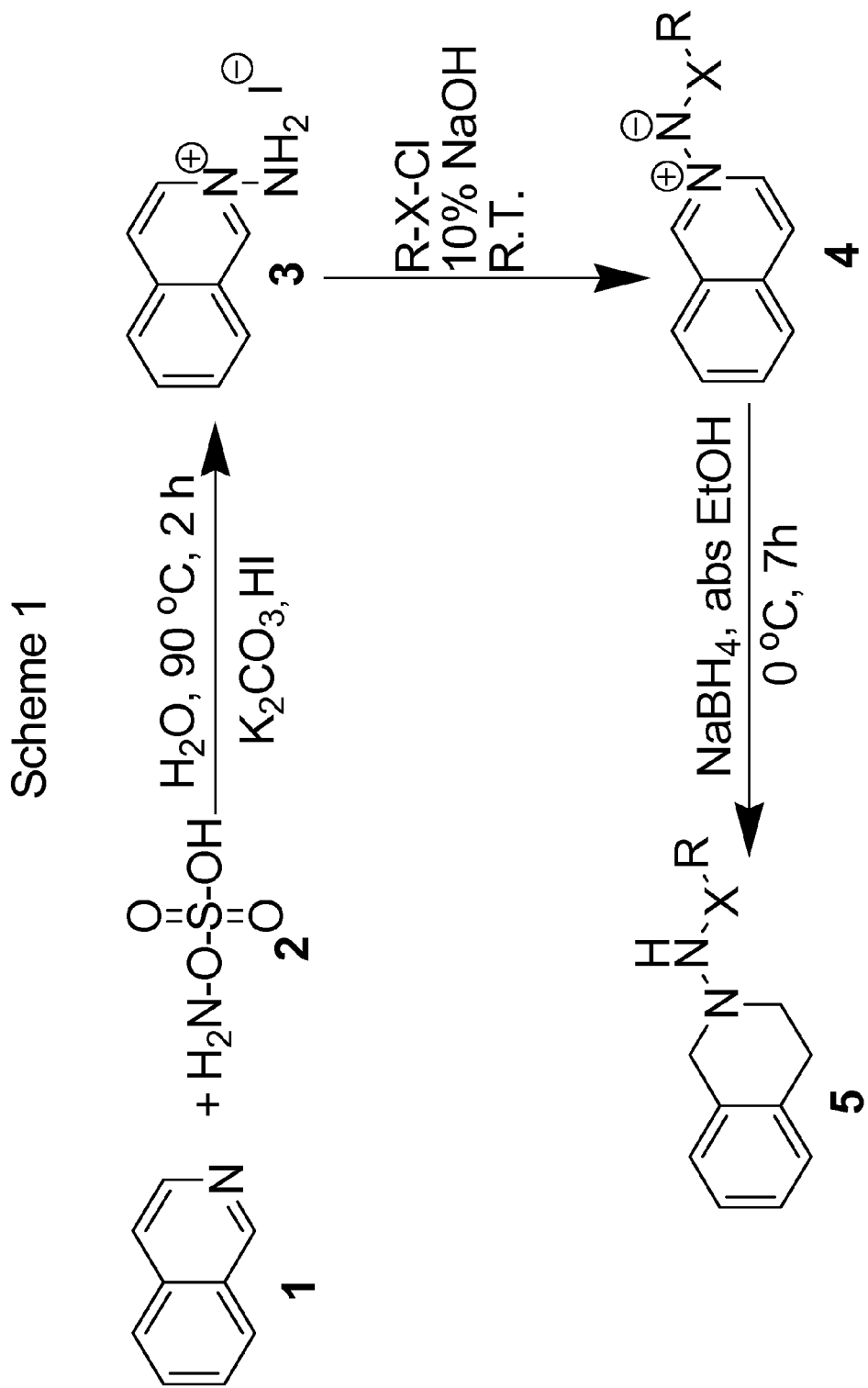
FIG. 1 schematically illustrates the synthesis of substituted N-(3,4-dihydroisoquinolin-2-(1H)-yl)benzamide/benzene sulfonamides.
Figure 2:
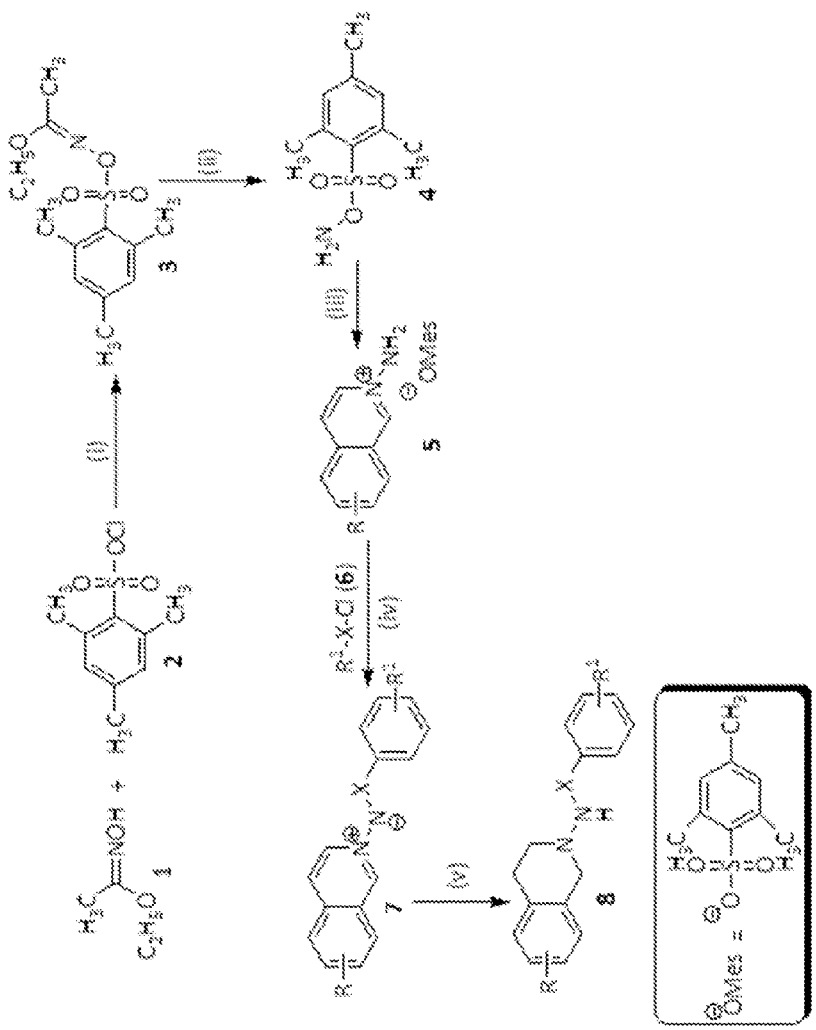
FIG. 2 schematically illustrates Scheme 2 for the synthesis of substituted 2-aminoisoqunilinium-2,4,6-trimethylbenzenesulfonate (5).
Figure 3:
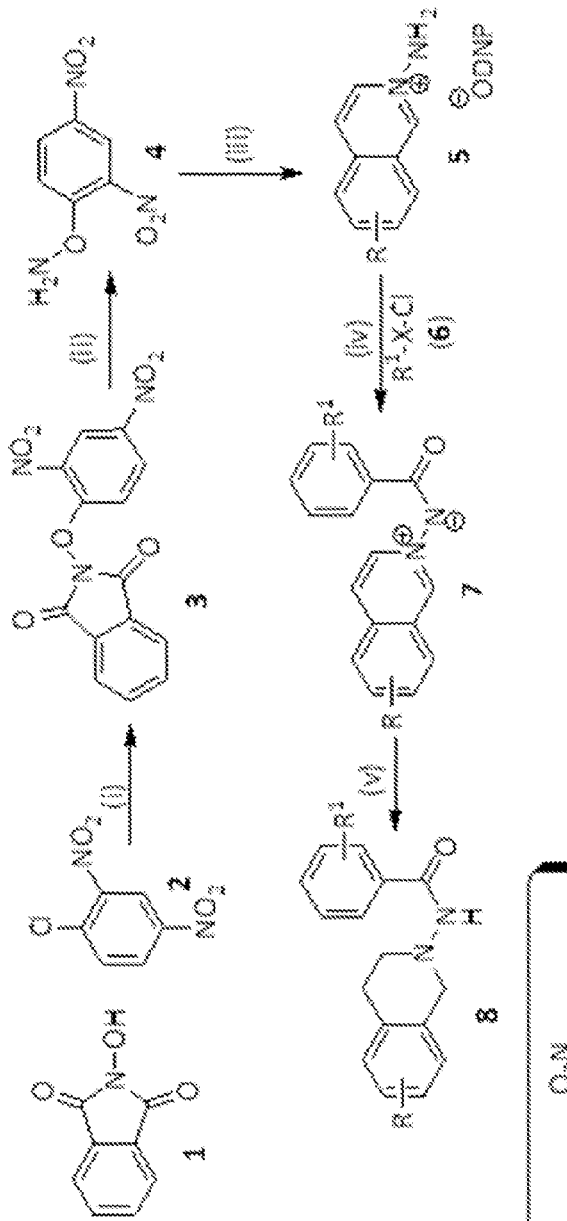
FIG. 3 schematically illustrates Scheme 3 for the synthesis of 2-aminoisoqunilinium-2,4-dinitrophenolate salt (4).

The drawings are described in greater detail in the description and examples below.

The details of some exemplary embodiments of the methods and systems of the present disclosure are set forth in the description below. Other features, objects, and advantages of the disclosure will be apparent to one of skill in the art upon examination of the following description, drawings, examples and embodiments. It is intended that all such additional systems, methods, features, and advantages be included within this description, be within the scope of the present disclosure.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended embodiments, the singular forms "a," "an," and "the" include plural referents unless the context clearly dictates otherwise. Thus, for example, reference to "a support" includes a plurality of supports. In this specification and in the embodiments that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein.

Prior to describing the various embodiments, the following definitions are provided and should be used unless otherwise indicated.

DEFINITIONS

The term "alkyl", either alone or within other terms such as "thioalkyl" and "arylalkyl", means a monovalent, saturated hydrocarbon radical which may be a straight chain (i.e. linear) or a branched chain. An alkyl radical for use in the present disclosure generally comprises from about 1 to 20 carbon atoms, particularly from about 1 to 10, 1 to 8 or 1 to 7, more particularly about 1 to 6 carbon atoms, or 3 to 6. Illustrative alkyl radicals include methyl, ethyl, n-propyl, n-butyl, n-pentyl, n-hexyl, isopropyl, isobutyl, isopentyl, amyl, sec-butyl, tert-butyl, tert-pentyl, n-heptyl, n-actyl, n-nonyl, n-decyl, undecyl, n-dodecyl, n-tetradecyl, pentadecyl, n-hexadecyl, heptadecyl, n-octadecyl, nonadecyl, eicosyl, dosyl, n-tetracosyl, and the like, along with branched variations thereof. In certain aspects of the disclosure an alkyl radical is a $C_1$-$C_6$ lower alkyl comprising or selected from the group consisting of methyl, ethyl, n-propyl, n-butyl, n-pentyl, n-hexyl, isopropyl, isobutyl, isopentyl, amyl, tributyl, sec-butyl, tert-butyl, tert-pentyl, and n-hexyl. An alkyl radical may be optionally substituted with substituents as defined herein at positions that do not significantly interfere with the preparation of compounds of the disclosure and do not significantly reduce the efficacy of the compounds. In certain aspects of the disclosure, an alkyl radical is substituted with one to five substituents including halo, lower alkoxy, lower aliphatic, a substituted lower aliphatic, hydroxy, cyano, nitro, thio, amino, keto, aldehyde, ester, amide, substituted amino, carboxyl, sulfonyl, sulfuryl, sulfenyl, sulfate, sulfoxide, substituted carboxyl, halogenated lower alkyl (e.g., $CF_3$), halogenated lower alkoxy, hydroxycarbonyl, lower alkoxycarbonyl, lower alkylcarbonyloxy, lower alkylcarbonylamino, cycloaliphatic, substituted cycloaliphatic, or aryl (e.g., phenylmethyl benzyl)), heteroaryl (e.g., pyridyl), and heterocyclic (e.g., piperidinyl, morpholinyl). Substituents on an alkyl group may themselves be substituted.

In aspects of the disclosure, "substituted alkyl" includes an alkyl group substituted by, for example, one to five substituents, and preferably 1 to 3 substituents, such as alkyl, alkoxy, oxo, alkanoyl, aryl, aralkyl, aryloxy, alkanoyloxy, cycloalkyl, acyl, amino, hydroxyamino, alkylamino, arylamino, alkoxyamino, aralkylamino, cyano, halogen, hydroxyl, carboxyl, carbamyl, carboxylalkyl, keto, thioketo, thiol, alkylthiol, arylthio, aralkylthio, sulfonamide, thioalkoxy; and nitro.

The term "halogen" as used herein refers to a halogen such as fluorine, chlorine, bromine or iodine atoms.

The term "hydroxyl" or "hydroxy" as used herein refers to an —OH group.

The term "alkoxy" refers to a linear or branched oxy-containing radical having an alkyl portion of one to about ten carbon atoms, such as a methoxy radical, which may be substituted. In aspects of the disclosure an alkoxy radical may comprise about 1-10, 1-8, 1-6 or 1-3 carbon atoms. In embodiments of the disclosure, an alkoxy radical comprises about 1-6 carbon atoms and includes a $C_1$-$C_6$ alkyl-O-radical wherein $C_1$-$C_6$ alkyl has the meaning set out herein. Examples of alkoxy radicals include without limitation methoxy, ethoxy, propoxy, butoxy, isopropoxy, and tert-butoxy alkyls. An "alkoxy" radical may, optionally be substituted with one or more substituents disclosed herein including alkyl atoms to provide "alkylalkoxy" radicals; halo atoms, such as fluoro, chloro or bromo, to provide "haloalkoxy" radicals (e.g., fluoromethoxy, chloromethoxy, trifluoromethoxy, difluoromethoxy, trifluoroethoxy, fluoroethoxy, tetrafluoroethoxy, pentafluoroethoxy, and fluoropropox) and "haloalkoxyalkyl" radicals (e.g., fluoromethoxymethyl, chloromethoxyethyl, trifluorornethoxymethyl, difluoromethoxyethyl, and trifluoroethoxymethyl).

The term "aryl", alone or in combination, as used herein refers to a carbocyclic aromatic system containing one, two or three rings wherein such rings may be attached together in a pendant manner or may be fused, in aspects of the disclosure an aryl radical comprises 4 to 24 carbon atoms, in particular 4 to 10, 4 to 8, or 4 to 6 carbon atoms. Illustrative "aryl" radicals includes without limitation aromatic radicals such as phenyl, benzyl, naphthyl, indenyl, benzocyclooctenyl, benzocycloheptenyl, pentalenyl, azulenyl, tetrahydronaphthyl, indanyl, biphenyl, acenaphthylenyl, fluorenyl, phenalenyl, phenanthrenyl, and anthracenyl, preferably phenyl.

An aryl radical may be optionally substituted with groups as disclosed herein, in particular hydroxyl, alkyl, carbonyl, carboxyl, thiol, amino, and/or halo, in particular a substituted aryl includes without limitation arylamine and arylalkylamine.

The term "substituted aryl" as used herein includes an aromatic ring, or fused aromatic ring system consisting of no more than three fused rings at least one of which is aromatic, and where at least one of the hydrogen atoms on a ring carbon has been replaced by a halogen, an amino, a hydroxy, a nitro, a thio, an alkyl, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, hydroxyphenyl, chlorphenyl and the like.

The term "carbonyl", whether used alone or with other terms, such as "aminocarbonyl", denotes —(C=O)—.

The term "cancer", as used herein shall be given its ordinary meaning and is a general term for diseases in which abnormal cells divide without control. Cancer cells can invade nearby tissues and can spread through the bloodstream and lymphatic system to other parts of the body. There are several main types of cancer, for example, carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma is cancer that begins in the cells of the immune system.

The term "composition" as used herein encompasses a product comprising the specified ingredients in the specified amounts, as well as any product that results, directly or indirectly, from combinations of the specified ingredients in the specified amounts.

"Pharmaceutically acceptable salts" include, but are not limited to, the acid addition salts of compounds of the present disclosure that are formed with inorganic acids (e.g., hydrochloric acid or phosphoric acids) and organic acids (e.g., acetic, oxalic, tartaric, or maleic acid). Salts formed with the free carboxyl groups may also be derived from inorganic bases (e.g., sodium, potassium, ammonium, calcium, or ferric hydroxides), and organic bases (e.g., isopropylamine, trimethylamine, 2-ethylamino-ethanol, histidine, and procaine).

The term "excipient" as used herein refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

The terms "effective amount" and "therapeutically-effective amount" as used herein mean that amount of a compound, material, or composition comprising a compound or composition of the present disclosure, and which is effective for producing a desired therapeutic effect, biological or medicinal response in a tissue system, animal or human that is being sought by a researcher, veterinarian, medical doctor or other clinician, which includes alleviation of the symptoms of the disease or disorder being treated.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or an encapsulating material such as liposomes, polyethylene glycol (PEG), PEGylated liposomes, nanoparticles and the like, involved in carrying or transporting the subject compositions or therapeutic agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include, but are not limited to: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

The terms "subject" and "animal or human subject" as used herein refers to any human or non-human animal to which a composition according to the disclosure may be delivered or administered.

Further definitions are provided in context below. Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein.

Discussion

The present disclosure encompasses embodiments of derivatives of N-substituted tetrahydroisoquinoline benzamides/benzene sulfonamides that have anti-proliferative activity against cells. In particular, although not intending to be limiting, the compounds of the disclosure have been found to be effective in inhibiting the proliferation of cancer cells, such as cancer cells that originated in breast tissue. Accordingly, it is contemplated that the compounds of the disclosure may be formulated into pharmaceutically effective compositions for delivery of the anti-proliferative compound to a cultured or in vivo cell, thereby reducing the proliferation of the cell or population of cells compared to the proliferation rate of the cells not exposed to the compound.

The compounds herein disclosed are analogs that maintain the integrity of the tetrahydroisoquinoline moiety, and have modifications on the phenyl rings by introducing groups with various electronic properties. The compounds were synthesized and characterized using NMR, IR and elemental analysis.

As schematically shown in FIG. 1, the starting compound 2-aminoisoquinolinium iodide (3) can be obtained by the reaction of isoquinoline and hydroxylamine-O-sulfonic acid and water with refluxing at 90° C. for about 2 h. Reaction of (3) with substituted acid chlorides or sulfonyl chlorides (4) in 10% KOH solution at room temperature gave stable ylides (5). Sodium borohydride reduction of (5) in absolute ethanol furnished the target compounds. It is contemplated that the reaction scheme as shown in FIG. 1 may incorporate the use of any substituted acid chloride or sulfonyl chloride, including, but not limited to, methanesulfonyl chloride, trifluoromethanesulfonyl chloride, ethanesulfonyl chloride, benzenesulfonyl chloride, p-toluenesulfonyl chloride, p-nitrobenzoyl chloride, benzoyl chloride, and the like.

The derivatives were examined for their cytotoxic effects on MCF-7 estrogen receptor-positive breast cancer cells, MDA-MB-231 estrogen receptor-negative breast cancer cell line, and Ishikawa cells, using the CELLTITER-GLO (CTG)® luminescent cell viability assay. All the compounds were tested in the three cell lines. Different concentrations of compounds, ranging from about 0.01 nM to about 100,000 nM were delivered to $5 \times 10^{-3}$ cells per well, which were then incubated for three days at 37° C., followed by CTG assay. $IC_{50}$ values were generated as shown in Table 1. These experiments showed that the compounds of the disclosure had $IC_{50}$ values against the target breast cancer cells that were 6-10-fold less than a currently clinically available anti-breast cancer therapy, Tamoxifen.

Accordingly, it is contemplated that the compounds of the present disclosure can be administered to a patient alone or as part of a pharmaceutically acceptable composition that contains other components such as excipients, diluents, and carriers, all of which are well-known in the art. The compositions can be administered to humans and animals either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethylene glycols, and the like. Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethylene glycols and fatty acid esters of sorbitan or mixtures of these substances, and the like. Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present disclosure with suitable non-irritating excipients or carriers such as cocoa butter, polyethylene glycol, or a suppository wax, which are solid at ordinary temperatures but liquid at body temperature and therefore, melt in the rectum or vaginal cavity and release the active component.

Dosage forms for topical administration of a compound of this disclosure include ointments, powders, sprays, and inhalants. The active component is admixed under sterile conditions with a physiologically acceptable carrier and any preservatives, buffers, or propellants as may be required.

Ophthalmic formulations, eye ointments, powders, and solutions are also contemplated as being within the scope of this disclosure.

The compounds of the present disclosure can be administered to a patient at dosage levels in the range of about 0.1 to about 2,000 mg per day. For a normal human adult having a body weight of about 70 kilograms, a dosage in the range of about 0.01 to about 100 mg per kilogram of body weight per day is preferable. The specific dosage used, however, can vary. For example, the dosage can depended on a numbers of factors including the requirements of the patient, the severity of the condition being treated, and the pharmacological activity of the compound being used. The determination of optimum dosages for a particular patient is well known to those skilled in the art.

The compounds of the present disclosure can exist in different stereoisomeric forms by virtue of the presence of asymmetric centers in the compounds. It is contemplated that all stereoisomeric forms of the compounds as well as mixtures thereof, including racemic mixtures, form part of this disclosure. In addition, the compounds of the present disclosure can exist in unsolvated as well as solvated forms with pharmaceutically acceptable solvents such as water, ethanol, and the like. In general, the solvated forms are considered equivalent to the unsolvated forms for the purposes of the present disclosure.

One aspect of the disclosure encompasses embodiments of a compound having the structure of formula I:

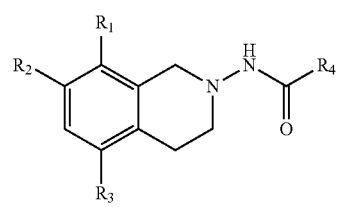

wherein: $R_1$ can be H or a halogen; $R_2$ can be H, an hydroxyl, or a carboxyalkyl; $R_3$ can be H, a halogen, or a carboxyalkyl, and wherein, when $R_3$ is a carboxyalkyl, $R_1$ is H; and $R_4$ is an alkylaryl or a benzothiazole; or a salt thereof.

In embodiments of this aspect of the disclosure, when $R_1$ or $R_2$ is a carboxyalkyl, said carboxyalkyl is —$OCH_3$.

In embodiments of this aspect of the disclosure, when $R_1$ or $R_1$ and $R_3$ are halogens, said halogen is Br.

In embodiments of this aspect of the disclosure, when the compound can be selected from the group consisting of:

Redda-GM-3-177

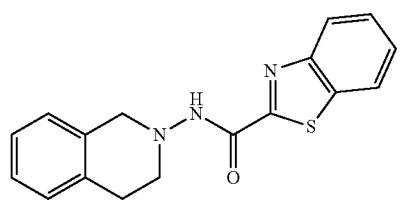

-continued

Redda-GM-4-62

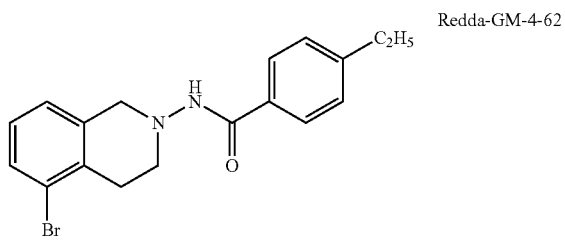

Redda-GM-4-53

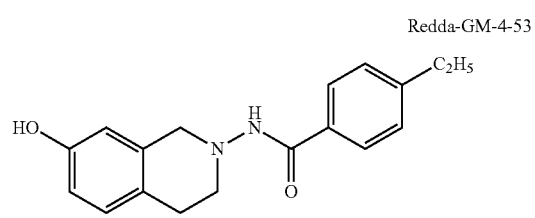

Redda-GM-4-40

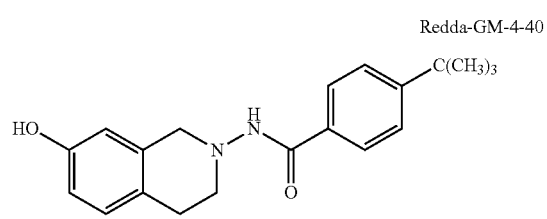

Redda-EVK-I-074

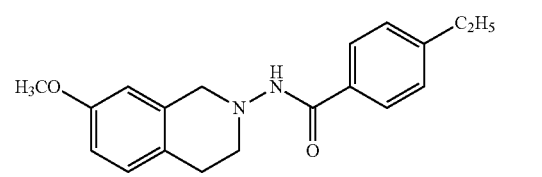

Redda-EVK-I-079

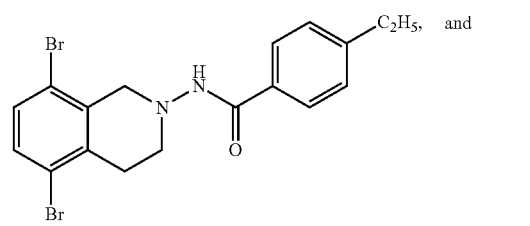

Redda-EVK-I-062

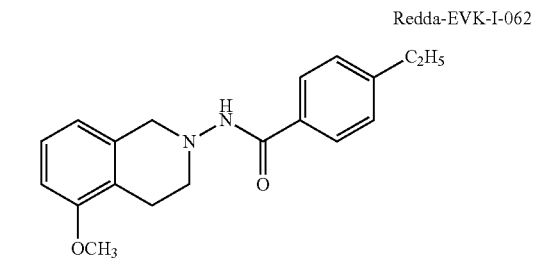

Another aspect of the disclosure encompasses embodiments of a pharmaceutically acceptable composition comprising a compound having the structure:

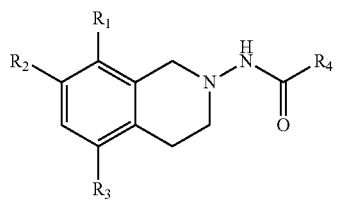

wherein: $R_1$ can be H or a halogen; $R_2$ can be H, an hydroxyl, or a carboxyalkyl; $R_3$ can be H, a halogen, or a carboxyalkyl, and wherein, when $R_3$ is a carboxyalkyl, $R_1$ is H; and $R_4$ is an alkylaryl or a benzothiazole; or a salt thereof.

In embodiments of this aspect of the disclosure, when $R_1$ or $R_2$ is a carboxyalkyl, said carboxyalkyl is —OCH$_3$.

In embodiments of this aspect of the disclosure, when $R_1$ or $R_1$ and $R_3$ are halogens, said halogen is Br.

In embodiments of this aspect of the disclosure, when the compound can be selected from the group consisting of:

Redda-GM-3-177

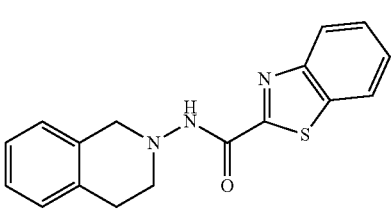

Redda-GM-4-62

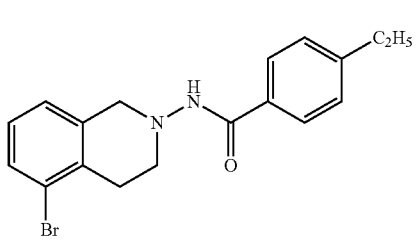

Redda-GM-4-53

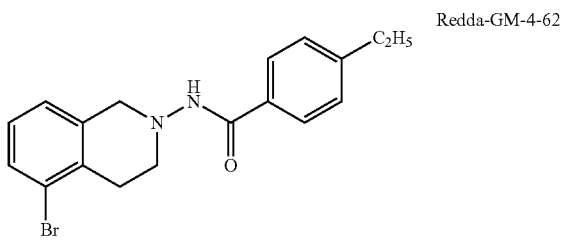

Redda-GM-4-40

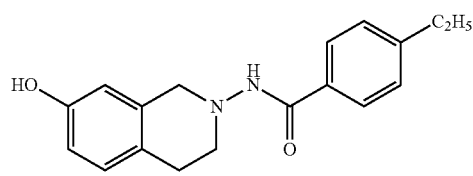

Redda-EVK-I-074

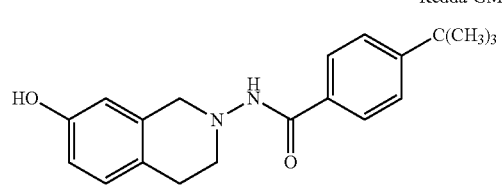

Redda-EVK-I-079

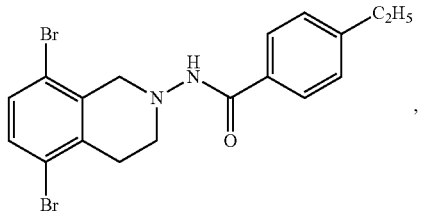

, and

Redda-EVK-I-062

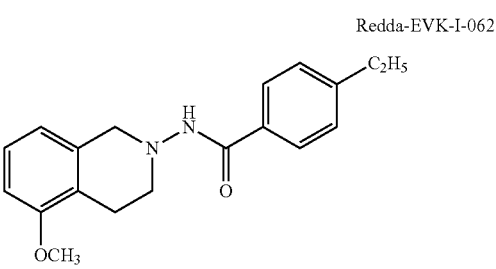

In embodiments of this aspect of the disclosure, the pharmaceutically acceptable composition can be formulated to provide an amount of the compound effective in inhibiting the proliferation of a cell cultured in vitro. In these embodiments, the cell can be a cancer cell. In some embodiments of this aspect of the disclosure, the cell can be a breast cancer cell.

In embodiments of this aspect of the disclosure, the pharmaceutically acceptable composition can be formulated to provide a therapeutically effective amount of the compound for inhibiting the proliferation of a cell in vivo. In some of these embodiments of this aspect of the disclosure the cell can be a cancer cell. In these embodiments of this aspect of the disclosure, the cell can be a breast cancer cell.

Still another aspect of the disclosure encompasses embodiments of a method of inhibiting the proliferation of a cell comprising contacting a cell with an effective amount of a compound having the structure:

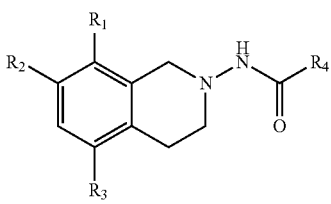

wherein:

$R_1$ is H or a halogen;

$R_2$ is H, an hydroxyl, or a carboxyalkyl;

$R_3$ is H, a halogen, or a carboxyalkyl, wherein, when $R_3$ is a carboxyalkyl, $R_1$ is H; and $R_4$ is an alkylaryl or a benzothiazole;

or a salt thereof, and a pharmaceutically acceptable carrier, thereby reducing the proliferation rate of the cell compared to the proliferation rate of a cell not in contact with the compound.

In embodiments of this aspect of the disclosure, the compound can be selected from the group consisting of:

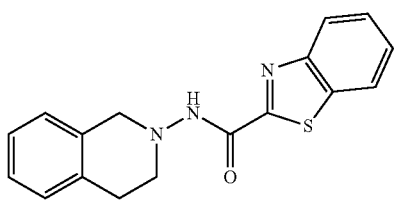
Redda-GM-3-177

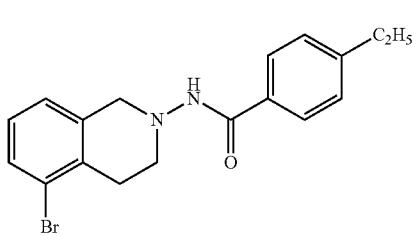
Redda-GM-4-62

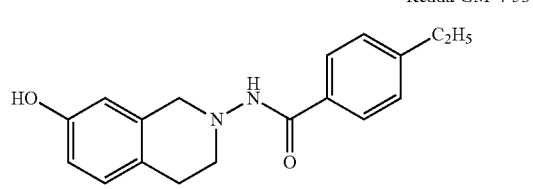
Redda-GM-4-53

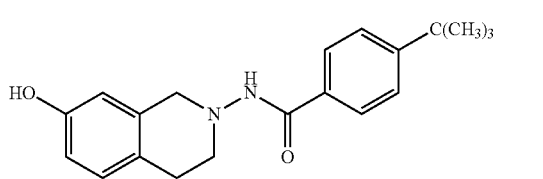
Redda-GM-4-40

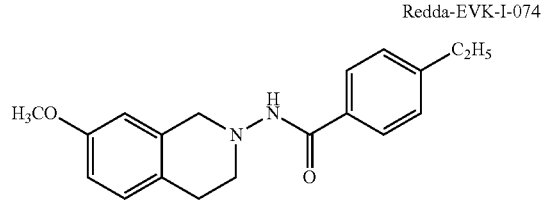
Redda-EVK-I-074

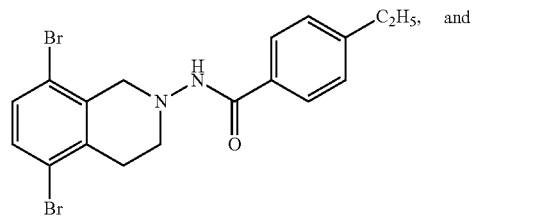
Redda-EVK-I-079 and

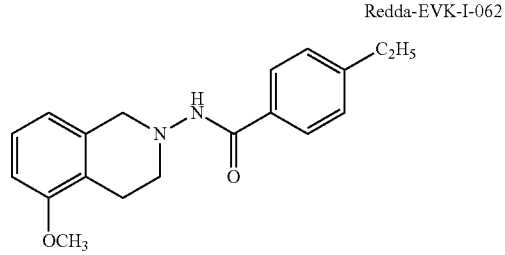
Redda-EVK-I-062

In embodiments of this aspect of the disclosure, the cell can be a breast cancer cell.

In embodiments of this aspect of the disclosure, the cell can be a cultured cell or a cell of an animal or human subject.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following embodiments.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

EXAMPLES

Example 1

Synthesis of 2-Aminoisoquinolinium Iodide (3)

A solution of hydroxylamine-O-sulfonic acid (2) (2 g, 1 equiv.), water (10 mL) and isoquinoline (1) (6.3 mL, 3 equiv.) was heated at 90° C. for 2-3 h. Potassium carbonate (2.44 g, 1 equiv.) was added, and the water was evaporated. Ethanol (20-30 mL) was added to the solid residue, and insoluble potassium sulfate was filtered out. Hydroiodic acid (57%-67%, 1.34 mL, 1 equiv.) was added to the filtrate, and the resulting solution was placed in a freezer. The precipitate was filtered out, washed with ethanol, and dried in vacuo. Isolated products were used as such in further reactions. Yield of the product was 1.78 g.

¹HNMR (CDCl₃) δ (ppm): 8.01 (td, J=7.2 Hz, 1H), 8.12 (td, J=7.2, 1.2 Hz, 1H), 8.30 (d, J=8.1 Hz, 1H), 8.43 (d, J=8.1 Hz, —NH₂, D₂O exchange), 8.50-8.57 (m, 4H), 9.69 (s, 1H).

Example 2

Synthesis of 2-amino-7-hydroxyisoquinolinium 2,4,6-trimethyl benzene-sulfonate (5)

O-mesitylene sulfonyl hydroxylamine (MSH) (3) was used to prepare the N-amino salt as an aminating agent as described by Tamura et al., (1972) *Tetrahedron Letter.* 40: 4133, incorporated herein by reference in its entirety. An ice cooled solution of 7-hydroxyisoquinoline (2.0 g, 13.78 mmol) in 30 mL of dry methylene chloride, and 15 ml of dry methanol was added drop wise to O-mesitylenesulfonylhydroxylamine (2.97 g, 13.78 mmol) in 10 mL of dry methylene chloride over 5 min with stirring. The reaction stirred at 0° C. for 6 h. 70 mL of ether was added and the suspension filtered. The precipitate was recrystallized from ethyl acetate to give 2-amino-7-hydroxyisoquinolinium 2,4,6-trimethylbenzene-sulfonate (6) in 60.5% yield.

Example 3

Synthesis of substituted 2-aminoisoquinolin-2-ium 2,4-dinitrophenolate salts (5)

2-(2,4-Dinitrophenoxy)-1H-isoindole-1,3(2H)-dione (3) was used to prepare the suitably N-amino salt, O-(2,4-dinitrophenyl)hydroxylamine (4) as an aminating agent (Legault & Charette (2003) *J. Org. Chem.* 68, 7119, incorporated herein by reference in its entirety). Acetonitrile (2 ml) was added to the suitably substituted isoquinolines (3 mmol) and the aminating salt, 0-(2,4-Dinitrophenyl)hydroxylamine (4) (3.41 mmol) in a sealed tube and the resulting suspension was heated at 50° C. for 24 h with vigorous stirring. Solvent evaporated from the resulting suspension and the solid obtained was washed with diethyl ether (3×15 ml). The resulting bright yellow solids were dried under high vacuum and used as such for the next reaction without purification. Yield (46-68%).

Example 4

Acylation

An ice-cold solution of substituted 2-aminoisoquinolinium salt (3,5) (8 mmol) in 25 ml of anhydrous tetrahydrofuran, was added to an substituted acid chloride or substituted benzenesulfonyl chloride (12 mmol) with stirring. The reaction was allowed to proceed for 12 h at 70° C. After cooling to room temperature the reaction was quenched by adding 25 ml of saturated aqueous sodium bicarbonate solution. The mixture was shaken repeatedly in separation funnel and allowed to stand for few minutes. Extraction with dichloromethane (2×100 ml), and drying over anhydrous sodium sulfate, and removal of the solvent in vacuo gave the crude product that was purified by combiflash chromatography using ethyl acetate:dichloromethane (3:2 v/v) as an eluent.

Example 5

Synthesis of 2-(4-Ethylbenzimido)isoquinolinium Ylide (5a)

2-Aminoisoquinolinium iodide (3, 2.5 g, 1 equiv.) was reacted with 4-ethylbenzoyl chloride (4.0 mL, 3 equiv.) in 30 ml of anhydrous tetrahydrofuran (THF) containing triethylamine at 70° C. was refluxed for 12 h. After completion of the reaction 30 mL of saturated sodium bicarbonate was added to arrested the reaction. The product was extracted with dichloromethane and dried over anhydrous sodium sulfate, filtered, and solvent was removed in vacuo to give the crude product, which was purified by combiflash chromatography using ethylacetate:dichloromethane (2:3 v/v) as an eluent. The resultant product was obtained as an off-white solid in 65% yield.

¹HNMR (CDCl₃) δ (ppm): 1.25 (t, 3H, J=7.5 Hz, —CH₂—CH₃), 2.66-2.73 (q, 2H, J=7.2 Hz, —CH₂—CH₃), 7.29 (d, 1H, J=8.4 Hz, $C_6$—H) 7.79-7.85 (m, 1H, $C_7$—H), 7.93-8.03 (m, 4H, $C_5$, $C_8$, $C_{3'}$, $C_{5'}$—H), 8.12-8.17 (m, 3H, $C_4$, $C_{2'}$, $C_{6'}$—H), 8.46 (dd, 1H, J=1.2, 5.7 Hz, $C_3$—H), 9.87 (s, 1H, $C_1$—H).

Example 6

Synthesis of 2-(4-Propylbenzimido)isoquinolinium Ylide (5b)

The compound 5b was obtained following General Procedure 2 as off-white solid in 53.0% yield.

¹HNMR (CDCl₃) δ (ppm): 0.94 (t, 3H, J=7.5 Hz, —CH₂—CH₂—CH₃), 1.61-1.71 (m, 2H, —CH₂—CH₂—CH₃), 2.64 (t, 2H, J=8.1 Hz, —CH₂—CH₂—CH₃), 7.24 (d, 1H, J=8.4 Hz, $C_6$—H) 7.79-7.85 (m, 1H, $C_7$—H), 7.91-7.94 (m, 2H, $C_5$, $C_8$—H), 7.99 (d, 2H, J=6.9 Hz, $C_{3'}$, $C_{5'}$—H), 8.11-8.15 (m, 3H, $C_4$, $C_{2'}$, $C_{6'}$—H), 8.45 (dd, 1H, J=1.5, 5.7 Hz, $C_3$—H), 9.87 (s, 1H, $C_1$—H).

Example 7

Synthesis of 2-(4-Bromobenzimido)isoquinolinium Ylide (5c)

The compound 5c was obtained following General Procedure 2 as light yellow solid in 58.6% yield.

¹HNMR (CDCl₃) δ (ppm): 7.38-7.47 (m, 2H, $C_6$, $C_7$—H), 7.78 (dd, 2H, J=1.2, 6.7 Hz, $C_{3'}$, $C_{5'}$—H), 7.84-7.91 (m, 1H, $C_5$—H), 7.99-8.17 (m, 4H, $C_4$, $C_8$, $C_{2'}$, $C_{6'}$—H), 8.24 (dd, 1H, J=1.2, 8.7 Hz, $C_3$—H), 9.39 (s, 1H, $C_1$—H).

Example 8

Synthesis of 2-(4-Trifluoromethylbenzimido)isoquinolinium Ylide (5d)

The compound 5d was obtained following General Procedure 2 as yellow solid in 68.4% yield.

¹HNMR (CDCl₃) δ (ppm): 7.69 (d, 2H, J=8.1 Hz, $C_{3'}$, $C_{5'}$—H), 7.82 (dtd, 1H, J=1.2, 1.5, 0.9 Hz, $C_7$—H), 7.89-8.01 (m, 3H, $C_5$, $C_6$, $C_8$—H), 8.08 (d, 1H, J=7.8 Hz, $C_4$—H), 8.31 (d, 2H, J=8.1 Hz, $C_{2'}$, $C_{6'}$, —H), 8.43 (dd, 1H, J=1.2, 5.7 Hz, $C_3$—H), 9.92 (s, 1H, $C_1$—H).

Example 9

Synthesis of 2-(4-n-Butylbenzimido)isoquinolinium Ylide (5e)

The compound 5e was obtained following General Procedure 2 as white solid in 60% yield.

¹HNMR (CDCl₃) δ (ppm): 0.92 (t, 3H, J=6.9 Hz, CH₂—CH₂—CH₂—CH₃), 1.30-1.42 (m, 2H, CH₂—CH₂—CH₂—

CH$_3$), 1.57-1.67 (m, 2H, CH$_2$—CH$_2$—CH$_2$—CH$_3$), 2.67 (t, 2H, J=7.8 Hz, CH$_2$—CH$_2$—CH$_2$—CH$_3$), 7.24 (d, 2H, J=9.0 Hz, C$_{3'}$, C$_{5'}$—H), 7.79-7.85 (m, 1H, C$_7$—H), 7.91-7.96 (m, 1H, C$_8$—H), 7.98 (d, 2H, J=6.9 Hz, C$_{2'}$, C$_{6'}$—H), 8.09-8.16 (m, 3H, C$_4$, C$_5$, C$_6$—H), 8.45 (dd, 1H, J=1.5, 5.7 Hz, C$_3$—H), 9.88 (s, 1H, C$_1$—H).

Example 10

Synthesis of (Benzo[d]thiazole-2-carbonyl)(isoquinolinium-2yl)imide Ylide (5f)

The compound 5f was obtained following General Procedure 2 as off white solid in 63% yield.

$^1$HNMR (CDCl$_3$) δ (ppm): 7.32-7.34 (m, 1H, C$_{8'}$—H), 7.47-7.52 (m, 1H, C$_{7'}$—H), 8.01-8.09 (m, 2H, C$_6$, C$_8$—H), 8.10-8.15 (m, 2H, C$_4$, C$_{6'}$—H), 8.20 (dd, 1H, J=1.5, 5.7 Hz, C$_{9'}$—H), 8.24 (d, 1H, J=6.2 Hz, C$_5$—H), 8.47 (dd, 1H, J=1.5, 5.7 Hz, C$_3$—H), 9.87 (s, 1H, C$_1$—H).

Example 11

Synthesis of (5-Bromoisoquinolinium-2-yl)-4-ethylbenzimide Ylide (7a)

The compound 7a was obtained following General Procedure 2 as yellow solid in 65% yield.

$^1$HNMR (CDCl$_3$) δ (ppm): 1.27 (t, 3H, J=7.5 Hz, —CH$_2$—CH$_3$), 2.66-2.75 (q, 2H, J=8.1, 7.8 Hz, —CH$_2$—CH$_3$), 7.25-7.29 (m, 3H, C$_5$, C$_{3'}$, C$_{5'}$—H), 7.67 (t, 1H, J=8.1 Hz, C$_7$—H), 8.07-8.18, (m, 3H, C$_8$, C$_{2'}$, C$_{6'}$—H), 8.32 (d, 1H, J=7.8 Hz, C$_4$—H), 8.54 (d, 1H, J=6.6 Hz, C$_3$—H), 10.17 (s, 1H, C$_1$—H).

Example 12

Synthesis of (4-Ethylbenzoyl)(7-hydroxyisoquinolinium-2yl)imide Ylide (7b)

The compound 7b was obtained following General Procedure 2 as light yellow solid in 50% yield.

$^1$HNMR (CDCl$_3$) δ (ppm): 1.26 (t, 3H, J=7.5 Hz, —CH$_2$—CH$_3$), 2.66-2.75 (q, 2H, J=8.1, 7.8 Hz, —CH$_2$—CH$_3$), 7.28 (d, 2H, J=8.7 Hz, C$_{3'}$, C$_{5'}$—H), 7.39 (d, 1H, J=2.1 Hz, C$_8$—H), 7.84 (d, 1H, J=5.7 Hz, C$_6$—H), 7.99 (d, 1H, J=2.1 Hz, C$_5$—H), 8.05 (d, 2H, J=8.1 Hz, C$_4$—H), 8.17 (d, 2H, J=8.4 Hz, C$_{2'}$, C$_{6'}$—H), 8.51 (d, 1H, J=6.0 Hz, C$_3$—H), 9.9 (s, 1H, C$_1$—H).

Example 13

Synthesis of (4-(tert-Butyl)benzoyl)(7-hydroxy isoquinolinium-2yl)imide Ylide (7c)

The compound 7c was obtained following General Procedure 2 as white solid in 60% yield.

$^1$HNMR (CDCl$_3$) δ (ppm): 1.38 (s, 9H, tert-butyl), 7.57 (d, 2H, J=8.7 Hz, C$_{3'}$, C$_{5'}$—H), 7.60 (d, 1H, J=2.1 Hz, C$_8$—H), 7.71 (d, 1H, J=5.7 Hz, C$_6$—H), 7.85 (d, 1H, J=2.1 Hz, C$_5$—H), 7.90 (d, 2H, J=8.7 Hz, C$_4$—H), 8.17 ((d, 2H, J=8.4 Hz, C$_{2'}$, C$_{6'}$—H), 8.55 (d, 1H, J=6.0 Hz, C$_3$—H), 9.27 (s, 1H, C$_1$—H).

Example 14

Synthesis of (4-Ethylbenzoyl)(7-methoxyisoquinolin-2-ium-2-yl)imide Ylide (7f)

The compound 7f was obtained following General Procedure 2 as white solid in 39% yield.

$^1$HNMR (CDCl$_3$) δ (ppm): 1.25 (t, 3H, J=7.5 Hz, —CH$_2$—CH$_3$), 2.69 (q, 2H, J=7.5 Hz, —CH$_2$—CH$_3$), 3.91 (s, 3H, —OCH$_3$), 7.18-7.21 (m, 3H), 7.47 (dd, 2H, J=9, 2.1 Hz), 7.77 (d, 2H, J=8.7 Hz), 8.07 (d, 2H, J=7.8 Hz), 8.20 (d, 1H, J=6.3 Hz), 9.57 (s, 1H, C$_1$—H).

Example 15

Synthesis of (5,8-Dibromoisoquinolinium-2-yl)(4-ethylbenzoyl)imide Ylide (7e)

The compound 7e was obtained following General Procedure 2 as white solid in 39% yield.

$^1$HNMR (CDCl$_3$) δ (ppm): 1.27 (t, 3H, J=7.8 Hz, —CH$_2$—CH$_3$), 2.73 (q, 2H, J=7.5 Hz, —CH$_2$—CH$_3$), 7.25-7.29 (m, 4H), 7.87-7.98 (m, 2H), 8.15 (d, 2H, J=8.1 Hz), 8.30 (d, 1H, J=7.5 Hz, 8.67 (dd, 1H, J=7.5, 1.5 Hz), 10.53 (s, 1H, C$_1$—H).

Example 16

Synthesis of (4-Ethylbenzoyl)(5-methoxyisoquinolinium-2-yl)imide Ylide (7d)

The compound 7d was obtained following General Procedure 2 as white solid in 27% yield.

$^1$HNMR (CDCl$_3$) δ (ppm): 1.25 (t, 3H, J=7.5 Hz, —CH$_2$—CH$_3$), 2.71 (q, 2H, J=7.5 Hz, —CH$_2$—CH$_3$), 4.05 (s, 3H, —OCH$_3$), 7.16 (d, 1H, J=7.5 Hz), 2.24 (d, 2H, J=8.1 Hz), 7.58-7.71 (m, 2H), 8.13 (d, J=8.4 Hz), 8.36 (m, 2H), 9.76 (s, 1H, C$_1$—H).

Example 17

Reduction

A solution of Ylide (5 mmol) in 20 ml of absolute ethanol was added drop-wise to a solution of sodium borohydride (50 mmol) in 25 ml of absolute ethanol pre-cooled to 0° C. The reaction was allowed to proceed for 5-7 h at 0° C. with stirring. Water (35 ml) was added, and allowed to warm up to room temperature. Extraction with dichloromethane (3×50 ml), drying over anhydrous sodium sulfate, and removal of the solvent in vacuo gave the crude product, which was purified by combiflash chromatography using ethyl acetate: dichloromethane (2:3 v/v) as an eluent to afford pure substituted THIQs.

Example 18

Synthesis of N-(3,4-Dihydroisoquinolin-2(1H)-yl)-4-ethylbenzamide (Redda-GM-3-121)

A solution of 2-(4-ethylbenzimido)isoquinolinium Ylide, 5a (0.7 g, 1 equiv.) in 20 mL absolute ethanol was added drop wise to a stirred suspension of sodium borohydride (0.43 g, 4 equiv.) in 20 ml of ethanol over a period or 30 min. The resulting solution was stirred for 7 h at 0° C. The reaction mixture was treated with 10 g of ice and allowed to warm up to 25° C. The product was extracted with dichloromethane (500 ml) and dried over anhydrous sodium sulfate. The dichloromethane filtrate was evaporated in vacuo and the product chromatographed on a combiflash using ethyl acetate:hexane (3:2 v/v) as an eluent to furnish Redda-GM-3-121 as a white solid 58.8% yield.

$^1$HNMR (CDCl$_3$) δ (ppm): 1.24 (t, 3H, J=7.5 Hz, —CH$_2$—CH$_3$), 2.64-2.72 (q, 2H, J=7.8 Hz, —CH$_2$—CH$_3$), 3.06 (t, 2H, J=6.0 Hz, C$_4$—H), 3.31 (t, 2H, J=5.7 Hz, C$_3$—H), 4.19 (s, 2H, C$_1$—H), 7.01 (d, 1H, J=2.4 Hz, C$_7$—H), 7.03 (s, 1H, —NH, D$_2$O exchange), 7.13-7.18 (m, 3H, C$_5$, C$_6$, C$_8$—H), 7.24 (d, 2H, J=8.1 Hz, C$_{3'}$, C$_{5'}$—H), 7.67 (d, 2H, J=8.1 Hz, C$_{2'}$, C$_{6'}$—H).

Example 19

Synthesis of N-(3,4-Dihydroxyisoquinolin-2(1H)-yl)-4-propylbenzamide (Redda-GM-3-122)

The compound Redda-GM-122 was obtained following General Procedure 3 as a white solid in 64.3% yield.

$^1$HNMR (CDCl$_3$) δ (ppm): 0.92 (t, 3H, J=7.2 Hz, —CH$_2$—CH$_2$—CH$_3$), 1.59-1.66 (m, 2H, —CH$_2$—CH$_2$—CH$_3$), 2.61 (t, 2H, J=8.1 Hz, —CH$_2$—CH$_2$—CH$_3$), 3.15 (t, 2H, J=5.7 Hz, C$_4$—H), 3.66 (t, 2H, J=5.7 Hz, C$_3$—H), 4.54 (s, 2H, C$_1$—H), 6.99 (d, 1H, J=6.6 Hz, C$_7$—H), 7.18 (s, 1H, —NH, D$_2$O exchange), 7.13-7.18 (m, 3H, C$_5$, C$_6$, C$_8$—H), 7.21 (d, 2H, J=8.4 Hz, C$_{3'}$, C$_{5'}$—H), 7.75 (d, 2H, J=8.4 Hz, C$_{2'}$, C$_{6'}$—H).

Example 20

Synthesis of 4-Bromo-N-(3,4-dihydroisoquinolin-2(1H)-yl)benzamide (Redda-GM-3-135)

The compound Redda-GM-3-135 was obtained following General Procedure 3 as a white solid in 55.6% yield.

$^1$HNMR (CDCl$_3$) δ (ppm): 3.07 (t, 2H, J=5.7 Hz, C$_4$—H), 3.32 (t, 2H, J=6.0 Hz, C$_3$—H), 4.19 (s, 2H, C$_1$—H), 7.02 (d, 1H, J=2.4 Hz, C$_7$—H), 7.04 (s, 1H, —NH, D$_2$O exchange), 7.14-7.19 (m, 3H, C$_5$, C$_6$, C$_8$—H), 7.26 (d, 2H, J=8.2 Hz, C$_{3'}$, C$_{5'}$—H), 7.69 (d, 2H, J=8.1 Hz, C$_{2'}$, C$_{6'}$—H).

Example 21

Synthesis of N-(3,4-Dihydroisoquinolin-2-(1H)-yl)-4-(trifluoromethyl)benzamide (Redda-GM-3-143)

The compound Redda-GM-3-143 was obtained following General Procedure 3 as a white solid in 60.4% yield.

$^1$HNMR (CDCl$_3$) δ (ppm): 3.07 (t, 2H, J=6.0 Hz, C$_4$—H), 3.35 (t, 2H, J=5.7 Hz, C$_3$—H), 4.21 (s, 1H, C$_1$—H), 7.03 (d, 1H, J=5.7 Hz, C$_7$H), 7.14 (s, 1H, —NH, D$_2$O exchange), 7.16-7.19 (m, 3H, C$_5$, C$_6$, C$_8$—H), 7.69 (d, 2H, J=8.1 Hz, C$_{3'}$, C$_{5'}$—H), 7.86 (d, 2H, J=8.1 Hz, C$_{2'}$, C$_{6'}$—H).

Example 22

Synthesis of 4-Butyl-N-(3,4-dihydrozyisoquinolin-2(1H)-yl)benzamide (Redda-GM-3-156)

The compound Redda-GM-3-156 was obtained following General Procedure 3 as a white solid in 60.4% yield.

0.92 (t, 3H, J=6.9 Hz, CH$_2$—CH$_2$—CH$_2$—CH$_3$), 1.30-1.42 (m, 2H, CH$_2$—CH$_2$—CH$_2$—CH$_3$), 1.57-1.67 (m, 2H, CH$_2$—CH$_2$—CH$_2$—CH$_3$), 2.67 (t, 2H, J=7.8 Hz, CH$_2$—CH$_2$—CH$_2$—CH$_3$), 3.06 (t, 2H, J=6.0 Hz, C$_4$—H), 3.31 (t, 2H, J=5.7 Hz, C$_3$—H), 4.19 (s, 2H, C$_1$—H), 7.01 (d, 1H, J=2.4 Hz, C$_7$—H), 7.03 (s, 1H, —NH, D$_2$O exchange), 7.13-7.18 (m, 3H, C$_5$, C$_6$, C$_8$—H), 7.28 (d, 2H, J=8.1 Hz, C$_{3'}$, C$_{5'}$—H), 7.64 (d, 2H, J=8.1 Hz, C$_{2'}$, C$_{6'}$—H).

Example 23

Synthesis of N-(3,4-Dihydroisoquinolin-2-(1H)-yl)benzo[d]thiazole-2-carboxamide (Redda-GM-3-177)

The compound Redda-GM-3-177 was obtained following General Procedure 3 as a white solid in 59.0% yield.

$^1$HNMR (CDCl$_3$) δ (ppm): 3.12 (t, 2H, J=6.0 Hz, C$_4$—H), 3.39 (t, 2H, J=6.0 Hz, C$_3$—H), 4.28 (s, 2H, C$_1$—H), 7.03 (d, 1H, J=1.8 Hz, C$_7$—H), 7.14-7.21 (m, 3H, C$_5$, C$_6$, C$_8$—H), 7.47-7.58 (m, 2H, C$_7$, C$_8$—H), 7.97-8.03 (m, 1H, C$_{9'}$—H), 8.05-8.08 (m, 1H, C$_{6'}$—H), 8.51 (s, 1H, —NH, D$_2$O exchange).

Example 24

Synthesis of N-(5-Bromo-3,4-dihyroisoquinolin-2(1H)-yl)-4-ethylbenzamide (Redda-GM-4-62)

The compound Redda-GM-4-62 was obtained following General Procedure 3 as a white solid in 65.0% yield.

$^1$HNMR (CDCl$_3$) δ (ppm): 1.18 (t, 3H, J=7.5 Hz, —CH2-CH3), 2.64-2.72 (q, 2H, J=7.5 Hz, —CH2-CH3), 2.86 (t, 2H, J=6.0 Hz, C$_4$—H), 3.18 (t, 2H, J=5.7 Hz, C$_3$—H), 3.94 (s, 2H, C$_1$—H), 6.35 (d, 1H, J=2.1, 1.8 Hz, C$_8$—H), 6.58 (dd, 1H, J=2.7, 5.4 Hz, C$_6$—H), 6.79 (d, 1H, J=8.4 Hz, C$_5$—H), 7.09 (s, 1H, —NH, D$_2$O exchange), 7.17 (d, 2H, J=8.1 Hz, C$_{3'}$, C$_{5'}$—H), 7.65 (d, 2H, J=8.1 Hz, C$_{2'}$, C$_{6'}$—H).

Example 25

Synthesis of 4-Ethyl-N-(7-hydroxy-3,4-dihydroisoquinolin-2-(1H)-yl)benzamide (Redda-GM-4-53)

The compound Redda-GM-4-53 was obtained following General Procedure 3 as a white solid in 65.0% yield. $^1$HNMR (CDCl$_3$) δ (ppm): 1.18 (t, 3H, J=7.5 Hz, —CH2-CH3), 2.64-2.72 (q, 2H, J=7.5 Hz, —CH2-CH3), 2.86 (t, 2H, J=6.0 Hz, C$_4$—H), 3.18 (t, 2H, J=5.7 Hz, C$_3$—H), 3.94 (s, 2H, C$_1$—H), 6.35 (d, 1H, J=2.1, 1.8 Hz, C$_8$—H), 6.58 (dd, 1H, J=2.7, 5.4 Hz, C$_6$—H), 6.79 (d, 1H, J=8.4 Hz, C$_5$—H), 7.09 (s, 1H, —NH, D$_2$O exchange), 7.17 (d, 2H, J=8.1 Hz, C$_{3'}$, C$_{5'}$—H), 7.65 (d, 2H, J=8.1 Hz, C$_{2'}$, C$_{6'}$—H).

Example 26

Synthesis of 4-(tert-Butyl)-N-(7-hydroxy-3,4-dihydroisoquinolin-2(1H)-yl)benzamide (Redda-GM-4-40)

The compound Redda-GM-4-40 was obtained following General Procedure 3 as a white solid in 65.0% yield.

$^1$HNMR (CDCl$_3$) δ (ppm): 1.33 (s, 9H, t-butyl group), 2.93 (t, 2H, J=6.0 Hz, C$_4$—H), 3.27 (t, 2H, J=5.7 Hz, C$_3$—H), 4.02 (s, 2H, C$_1$—H), 6.43 (s, 1H, C$_8$—H), 6.66 (dd, 1H, J=2.7, 1.8 Hz, C$_6$—H), 6.84 (d, 1H, J=9.0 Hz, C$_5$—H), 7.09 (s, 1H, —NH, D$_2$O exchange), 7.47 (d, 2H, J=8.1 Hz, C$_{3'}$, C$_{5'}$—H), 7.73 (d, 2H, J=8.4 Hz, C$_{2'}$, C$_{6'}$—H).

Example 27

Synthesis of 4-Ethyl-N-(7-methoxy-3,4-dihydroisoquinolin-2(1H)-yl)benzamide (Redda-EVK-I-074)

The compound Redda-EVK-I-074 was obtained following General Procedure 3 as a white solid in 55% yield.

$^1$HNMR (CDCl$_3$) δ (ppm): 1.24 (t, J=7.8 Hz, 3H, —CH$_2$—CH$_3$), 2.72-2.64 (q, J=7.5 Hz, 2H, —CH$_2$—CH$_3$), 2.98 (t, J=6 Hz, 2H), 3.34 (t, J=5.7 Hz, 2H), 3.77 (s, 3H, —OCH$_3$), 4.18 (s (br), 2H), 6.55 (d, J=2.4 Hz), 6.77-6.73 (dd, J=8.4, 2.4 Hz, 1H), 7.06 (d, J=8.4 Hz, 1H), 7.26-7.23 (m, 2H), 7.68 (d, J=7.5 Hz).

Example 28

Synthesis of N-(5,8-Dibromo-3,4-dihydroisoquinolin-2(1H)-yl)-4-ethylbenzamide (Redda-EVK-I-079)

The compound Redda-EVK-I-0-79 was obtained following General Procedure 3 as a light yellow color solid in 61% yield.

$^1$HNMR (CDCl$_3$) δ (ppm): 1.24 (t, J=7.5 Hz, 3H, —CH$_2$—CH$_3$), 2.73-2.65 (q, J=7.8 Hz, 2H, —CH$_2$—CH$_3$), 3.30 (t, J=6 Hz, 2H), 3.34, t, J=6 Hz, 2H), 4.18 (s (br), 2H), 7.34-7.25 (m, 4H), 7.72 (d, J=7.8 Hz, 2H).

Example 29

Synthesis of 4-Ethyl-N-(5-methoxy-3,4-dihydroisoquinolin-2(1H)-yl)benzamide (Redda-EVK-I-062)

The compound Redda-EVK-I-0-62 was obtained following General Procedure 3 as a light yellow color solid in 52% yield.

$^1$HNMR (CDCl$_3$) δ (ppm): 1.23 (t, J=7.8 Hz, 3H, —CH$_2$—CH$_3$), 2.63-2.71 (q, J=7.8 Hz, 2H, —CH$_2$—CH$_3$), 2.92 (t, J=6.3 Hz, 2H), 3.35 (t, J=6.3 Hz, 2H), 3.82 (s, 3H, —OCH$_3$), 4.2 (s (br), 2H), 6.65 (d, J=7.5 Hz), 6.72 (d, J=8.1 Hz, 1H), 7.14 (t, J=8.1 Hz, 1H), 7.22-7.261 (m, 2H), 7.68 (d, J=8.4 Hz, 2H).

Example 30

Compounds Redda-GM-3-121, Redda-GM-3-122, Redda-GM-3-135, Redda-GM-3-156, Redda-GM-3-177, Redda-GM-4-62, Redda-GM-4-53, Redda-GM-4-40, Redda-EVK-1-074, Redda-EVK-1-079, and Redda-EVK-1-062 were tested for their cytotoxic effects on MCF-7 estrogen receptor-positive breast cancer cells, MDA-MB-231 estrogen receptor-negative breast cancer cell line, and Ishikawa cells, using the CELLTITER-GLO® luminescent cell viability assay (Promega, Madison, Wis.) following the manufacturer's instruction.

CELLTITER-GLO® is a homogeneous method based on the quantification of ATP, which is an indicator of metabolically active cells. In this assay, the number of viable cells in culture is determined based on the quantification of ATP present, which signals the presence of metabolically active cells. Damaged cells are not detected as the ATP leaked from these cells is quickly consumed by ATPases that are also released upon damage). The amount of ATP is determined using a system based on luciferase and D-luciferin resulting in light generation.

The cell lines were plated in 13, 96 well plates at a density of 5000 cells/well in total volumes of 50 μL in phenol-red free medium and incubated for overnight. Compounds Redda-GM-3-121, Redda-GM-3-122, Redda-GM-3-135, Redda-GM-3-156, Redda-GM-3-177, Redda-GM-4-62, Redda-GM-4-53, Redda-GM-4-40, Redda-EVK-1-074, Redda-EVK-1-079, and Redda-EVK-1-062 were weighed and dissolved in DMSO (10 mM) and tested at different concentrations ranging from 0.01 to 100,000 nM, using Tamoxifen (10 μAA) as a positive control.

25 μL of 40 nM estradiol should be added to all appropriate wells on the plate. 25 μL media were added to all wells that did not receive estradiol. 25 μL of stocks (containing the compounds to be tested, DMSO and phenol-red free medium) were added to cells and medium already on plate. 50 μL of medium were added to media wells, and 50 μL of mix (contain 32 mL DMSO+768 mL phenol-red free medium) to all vehicle control wells. Tamoxifen (10 μM) was also added to appropriate wells.

Drug-exposed cells were incubated or 72 h at 37° C. in a 5% CO$_2$ incubator, after which the plates were removed for CELLTITER-GLO® assay and equilibrated at room temperature for 30 min. 100 μL of CELLTITER-GLO® assay reagent was added to each well and cell-lysis was induced on an orbital shaker for 2 min. followed by a further 10 min incubation at room temperature. Luminescence results were read on TriLux Luminometer. The luminescent signal is proportional to the number of active cells present in culture. Dead cells did not affect cell counts because they did not contribute to ATP content. As a consequence, the number of metabolically active cells can be directly derived from the luminescent signal using a specific calibration curve. Data were expressed as percentage of untreated control (i.e. treatment value-blank/ vehicle value blank), mean±SE for three replications. The IC$_{50}$ values, as shown in Table 1, were determined using GraphPad Prism 4 dose-response curve fitting.

Table 1: In Vitro Anticancer Activity of Substituted Tetrahydroisoquinolines Against Breast Cancer Cell Lines

TABLE 1

In vitro anticancer activity of substituted tetrahydroisoquinolines against breast cancer cell lines

| CODE | STRUCTURE | IC$_{50}$ μg/mL | | |
|---|---|---|---|---|
| | | MCF-7 | ISHIKAWA | MDA-MB-231 |
| Redda-GM-3-121 | (structure) | 0.43 | 0.01 | 0.37 |

TABLE 1-continued

In vitro anticancer activity of substituted tetrahydroisoquinolines against breast cancer cell lines

| CODE | STRUCTURE | IC$_{50}$ µg/mL | | |
|---|---|---|---|---|
| | | MCF-7 | ISHIKAWA | MDA-MB-231 |
| Redda-GM-3-122 | 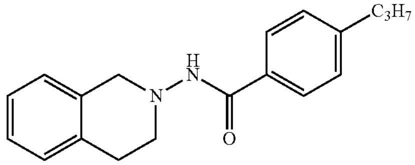 | 3.71 | 0.75 | 3.26 |
| Redda-GM-3-135 | 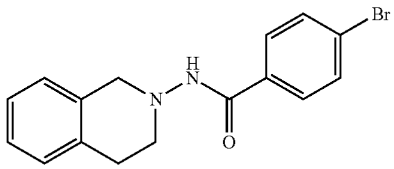 [SMILES: O=C(NN1CCc2ccccc2C1)c1ccc(Br)cc1] | 0.7 | 0.02 | 4.34 |
| Redda-GM-3-143 | 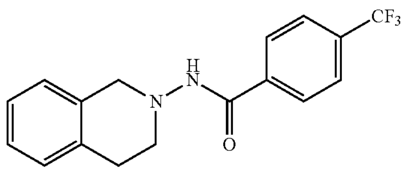 [SMILES: O=C(NN1CCc2ccccc2C1)c1ccc(C(F)(F)F)cc1] | 3.15 | 0.5 | 4.85 |
| Redda-GM-3-156 | 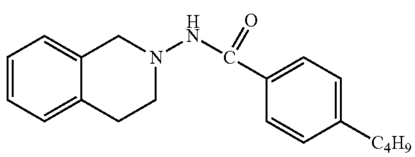 | 3.05 | 0.96 | 7.03 |
| Redda-GM-3-177 | 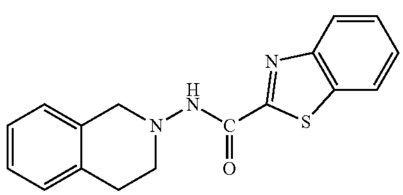 [SMILES: O=C(NN1CCc2ccccc2C1)c1nc2ccccc2s1] | 15.0 | 8.98 | 13.11 |
| Redda-GM-4-62 | 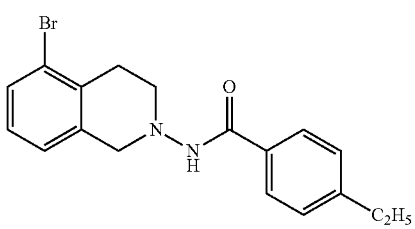 [SMILES: CCc1ccc(C(=O)NN2CCc3c(Br)cccc3C2)cc1] | 3.50 | 1.15 | 6.01 |
| Redda-GM-4-53 | 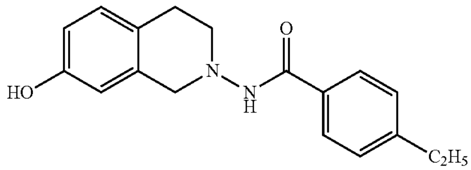 [SMILES: CCc1ccc(C(=O)NN2CCc3ccc(O)cc3C2)cc1] | 0.20 | 0.08 | 0.13 |
| Redda-GM-4-40 | 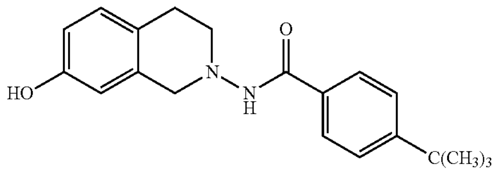 [SMILES: CC(C)(C)c1ccc(C(=O)NN2CCc3ccc(O)cc3C2)cc1] | 2.30 | 0.95 | 4.70 |

TABLE 1-continued

In vitro anticancer activity of substituted tetrahydroisoquinolines against breast cancer cell lines

| CODE | STRUCTURE | IC$_{50}$ µg/mL | | |
|---|---|---|---|---|
| | | MCF-7 | ISHIKAWA | MDA-MB-231 |
| Redda-EVK-I-074 | 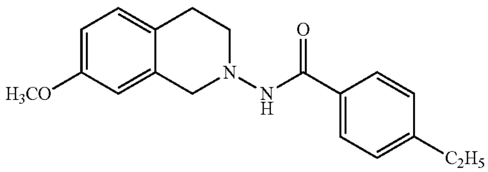 [SMILES: CCc1ccc(C(=O)NN2CCc3ccc(OC)cc3C2)cc1] | 0.25 | 0.11 | 0.23 |
| Redda-EVK-I-079 | 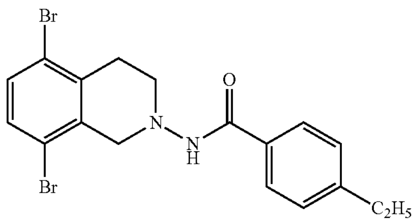 [SMILES: CCc1ccc(C(=O)NN2CCc3c(Br)ccc(Br)c3C2)cc1] | 2.34 | 0.84 | 1.71 |
| Redda-EVK-I-062 | 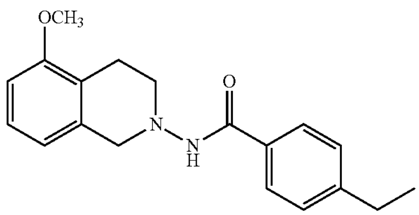 [SMILES: CCc1ccc(C(=O)NN2CCc3c(cccc3OC)C2)cc1] | 7.38 | 6.34 | 10.46 |
| Tamoxifen | 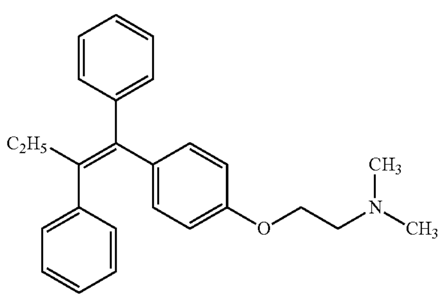 [SMILES: CC/C(=C(\c1ccccc1)c1ccc(OCCN(C)C)cc1)c1ccccc1] | 6.21 | 6.11 | 5.98 |

We claim:

1. A compound having the structure:

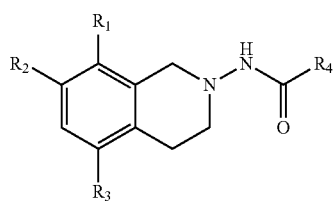

wherein:
R$_1$ is H or Br;
R$_2$ is H, an hydroxyl, or an alkoxy;
R$_3$ is H, a halogen, or an alkoxy, wherein, when R$_3$ is an alkoxy, R$_1$ is H, and
R$_4$ is an alkylaryl- group or a benzothiazole group; and
wherein if R$_1$, R$_2$, and R$_3$ are each H, R$_4$ is a benzothiazole group,
or a salt thereof.

2. The compound of claim 1, wherein R$_1$ or R$_2$ is —OCH$_3$.

3. The compound of claim 1, wherein said compound is selected from the group consisting of:

Redda-GM-3-177

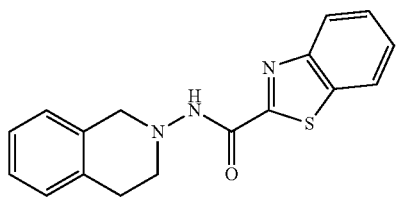

Redda-GM-4-62

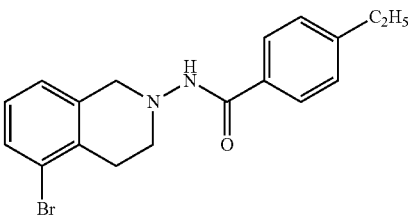

-continued

Redda-GM-4-53
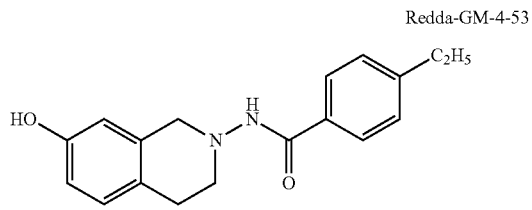

Redda-GM-4-40
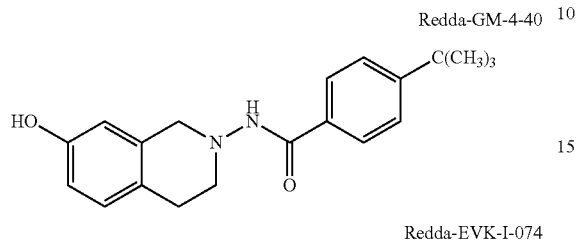

Redda-EVK-I-074
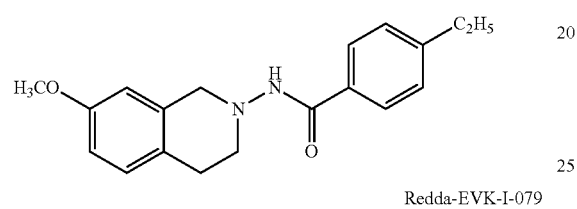

Redda-EVK-I-079
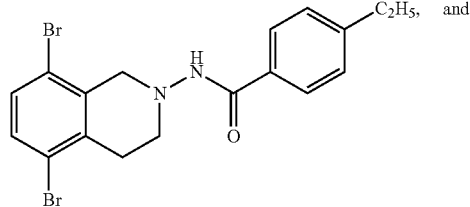

Redda-EVK-I-062
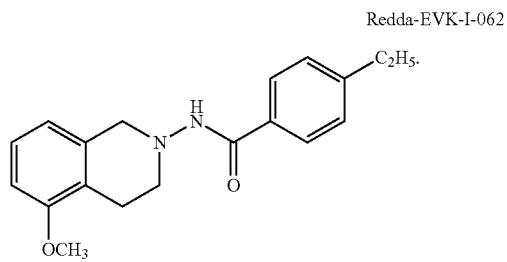

4. A pharmaceutically acceptable composition comprising a compound having the structure:

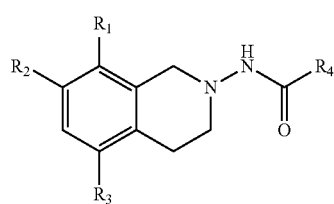

wherein:

R₁ is H or Br;

R₂ is H, hydroxyl or an alkoxy,

R₃ is H, a halogen or an alkoxy, wherein, when R₃ is an alkoxy, R₁ is H; and

R₄ is an alkylaryl- group or a benzothiazole;

wherein if R₁, R₂, and R₃ are each H, R₄ is a benzothiazole group, or a salt thereof, and a pharmaceutically acceptable carrier.

5. The pharmaceutically acceptable composition of claim 4, wherein the compound is selected from the group consisting of:

Redda-GM-3-177
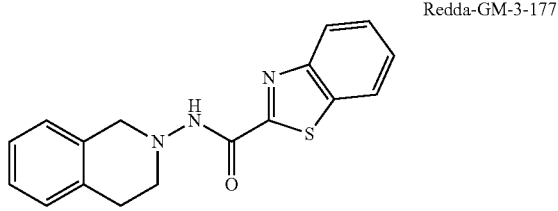

Redda-GM-4-62
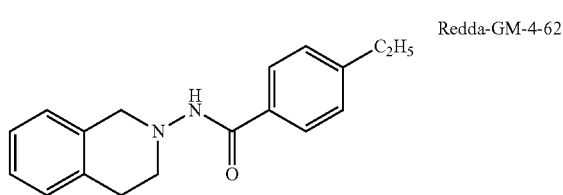

Redda-GM-4-53
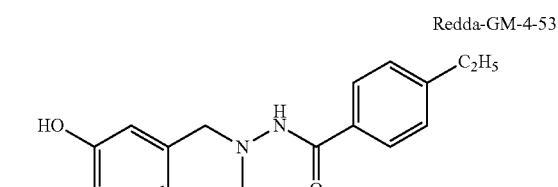

Redda-GM-4-40
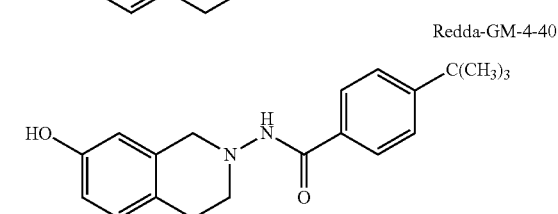

Redda-EVK-I-074
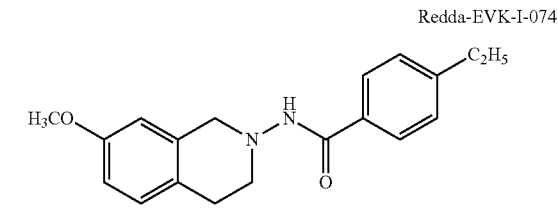

Redda-EVK-I-079
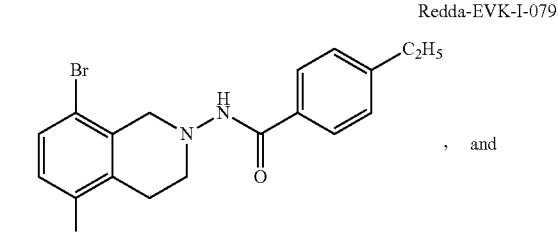

, and

-continued

Redda-EVK-I-062

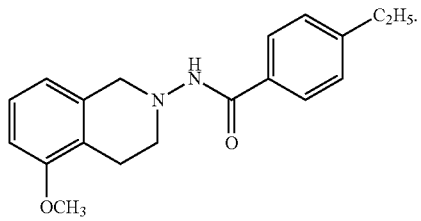

6. The pharmaceutically acceptable composition according to claim 4, wherein said pharmaceutically acceptable composition is formulated to provide an amount of the compound effective in inhibiting the proliferation of a cell cultured in vitro.

7. The pharmaceutically acceptable composition according to claim 6, wherein the cell is a cancer cell.

8. The pharmaceutically acceptable composition according to claim 6, wherein the cell is a breast cancer cell.

9. The pharmaceutically acceptable composition according to claim 7, wherein said pharmaceutically acceptable composition is formulated to provide a therapeutically effective amount of the compound for inhibiting the proliferation of a cell in vivo.

10. The pharmaceutically acceptable composition according to claim 9, wherein the cell is a cancer cell.

11. The pharmaceutically acceptable composition according to claim 9, wherein the cell is a breast cancer cell.

12. A method of inhibiting the proliferation of a cell comprising contacting a cell with an effective amount of a compound having the structure:

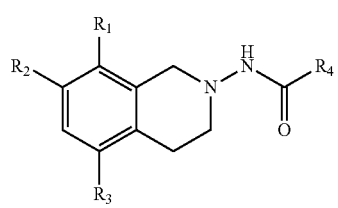

wherein:

$R_1$ is H or Br;

$R_2$ is H, an hydroxyl, or a alkoxy;

$R_3$ is H, a halogen, or a alkoxy, wherein, when $R_3$ is a alkoxy, $R_1$ is H; and $R_4$ is an alkylaryl- group or a benzothiazole group;

wherein if $R_1$, $R_2$, and $R_3$ are each H, $R_4$ is a benzothiazole group, or a salt thereof, and a pharmaceutically acceptable carrier, thereby reducing the proliferation rate of the cell compared to the proliferation rate of a cell not in contact with the compound.

13. The method of claim 12, wherein the compound is selected from the group consisting of:

Redda-GM-3-177

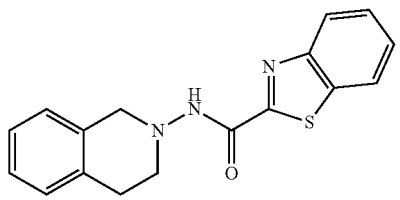

Redda-GM-4-62

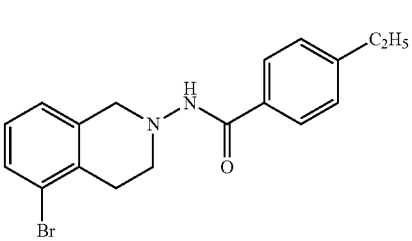

Redda-GM-4-53

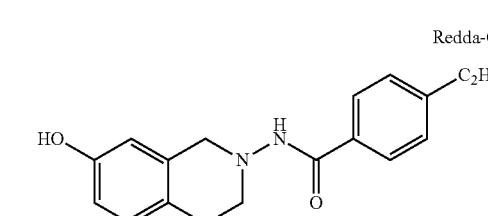

Redda-GM-4-40

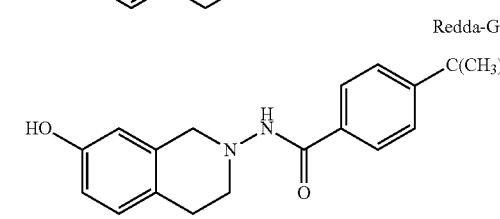

Redda-EVK-I-074

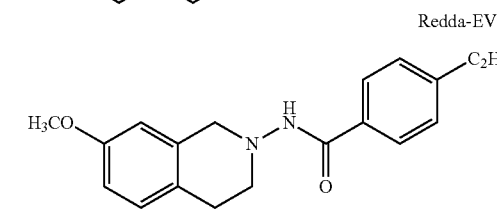

Redda-EVK-I-079

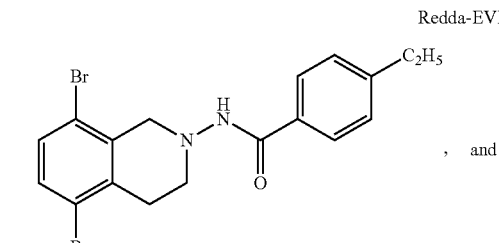

, and

Redda-EVK-I-062

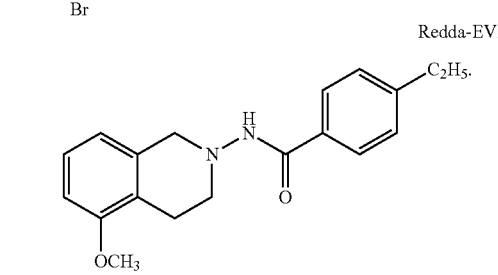

14. The method of claim 12, wherein the cell is a breast cancer cell.

15. The method of claim 12, wherein the cell is a cultured cell or a cell of an animal or human subject.

\* \* \* \* \*